United States Patent [19]
Gander et al.

[11] Patent Number: 5,023,330
[45] Date of Patent: Jun. 11, 1991

[54] PROCESS FOR PREPARING 1,6-β-D-ANHYDROGLUCOPYRANOSE (LEVOGLUCOSAN) IN HIGH PURITY

[75] Inventors: Michael Gander, Worms; Knut M. Rapp, Offstein; Hubert Schiweck, Worms, all of Fed. Rep. of Germany

[73] Assignee: Suedzucker-Aktiengesellschaft, Mannheim, Fed. Rep. of Germany

[21] Appl. No.: 302,885

[22] Filed: Jan. 30, 1989

[30] Foreign Application Priority Data

Feb. 4, 1988 [DE] Fed. Rep. of Germany ....... 3803339

[51] Int. Cl.$^5$ .................. C07H 3/10; C07H 19/00; C08B 37/00; C13K 13/00
[52] U.S. Cl. .................. 536/124; 536/127; 536/1.1
[58] Field of Search .................. 536/124, 127, 1.1

[56] References Cited

U.S. PATENT DOCUMENTS 3,235,541  2/1966  Carlson .................. 536/124
3,374,222  3/1968  Peniston .................. 536/127
3,478,012  11/1969  Wolff et al. .................. 536/124

FOREIGN PATENT DOCUMENTS 0229034  7/1987  European Pat. Off. .
3424217  1/1986  Fed. Rep. of Germany .

OTHER PUBLICATIONS

Carbohydr. Chem 34, 23 (1977).
Carbohydr. Res. 57, C31–C35 (1977).
"Stereoselective Synthesis", pp. 65, 79 (1987).
Polymer J. vol. 16, No. 3, pp. 297–301 (1984).
Chem. Abstr. 102, 95 916q.
Chem. Abstr. 101, 73 215n.
Chem. Abstr. 100, 175 205f.
Methods Carbohydr. Chem. 2, 397 (1963).
Methods Carbohydr. Chem. 2, 394 (1963).
Carbohydr. Res. 101, 148 (1982).
Chem. Abstr. 102, 204 235q (1985).
Comp. Phytochemistry 21, 2301 (1982).
Carbohydr. Res. 162, 141 (1987).
Chem. Abstr. 71, 82 868s.
Chem. Abstr. 104, 34 285c (1986).
Carbohydr. Chem. Biochem. 39, 157 (1981).

*Primary Examiner*—Ronald W. Griffin
*Assistant Examiner*—Everett White
*Attorney, Agent, or Firm*—Armstrong, Nikaido, Marmelstein, Kubovcik & Murray

[57] ABSTRACT

Process of preparing 1,6-β-D-anhydroglucopyranose (levoglucosan) in high purity is described, where the starting material with a water-content, adjusted to max. 20%, is pyrolyzed, the volatile components are condensed and this distillate is neutralized. After filtration and optional treatment with an adsorbent, the mixture is chromatographically separated over an ion-exchange resin with water as eluent. Levoglucosan containing fractions are concentrated and crystalline levoglucosan is obtained by an evaporation - and/or cooling crystallization from a supersaturated water solution.

20 Claims, 6 Drawing Sheets

TEMPERATURE/TIME-DIAGRAM OF A STARCH PYROLYSIS, $T_1$ IS THE TEMPERATURE MEASURED IN THE STARCHY MATERIAL, $T_2$ IS THE DISTILLATE TRANSITION TEMPERATURE

FIG. 1

PYROLYSIS APPARATUS:

RB = RING GAS BURNER
$T_1$, $T_2$ = POSITIONS FOR MEASURING THE TEMPERATURE
KW = COOLING WATER
P = PRESSURE MEASUREMENT
VP = VACUUM PUMP

FIG. 3

FIG. 5

PROCESS FOR PREPARING 1,6-β-D-ANHYDROGLUCOPYRANOSE (LEVOGLUCOSAN) IN HIGH PURITY

DESCRIPTION

Most of the chemical raw materials are produced today from petroleum. The finiteness of fossil reserves and the problem of utilisation of surplus products of the farming industry in the EG and the USA makes it necessary to utilize renewable resources for products, which are manufactured so far from petroleum.

As carbohydrates, besides sucrose, especially starch is suitable, for the annual corn production (70% starch) is comparable with the annual oil production ($\sim 10^9$ t).

Chemical raw materials have to be available today in large amounts and at acceptable prices. In a special degree they have to be produced in a simple and safe way, and in a way not adversely affecting the environment. Production processes have to be versatile, modifiable and applicable to a wide range of conditions, and the products produced thereby should be ecologically acceptable.

A product which can be simply produced and which conforms to the above mentioned criteria is 1,6-β-D-anhydroglucopyranose (levoglucosan) with the following structural formula.

Levoglucosan is hence a derivative of glucose, the most abundant sugar on earth.

The chemistry of 1,6-β-D-anhydroglucopyranose (levoglucosan) has long been known and its multiple reaction possibilities have been well examined (M. Černý and J. Staněk, Adv. Carbohydr. Chem. Biochem., 34, 23 (1977) Academic Press, New York, San Fransisco, London); a greater industrial utilisation of this product has not happened because there is no simple production means in a larger scale.

The synthetic potential of levoglucosan covers a broad area e.g. the synthesis of oligosaccharides or of (+)-biotin (Carbohydr. Res. 57, C31–C35 (1977)) and the possibility to make pharmaceuticals, e.g. cytostatica (DE-OS 34 24 217), or herbicidal or plant-growth regulating substances (EU 0 229 034) using it.

The chirality of levoglucosan makes it possible to synthesize the phosphinic ligand DIOXOP, which is a component of a catalyst for the diastereoselective hydrogenation (M. Nógrádi, Stereoselective Synthesis, VCH Verlagsgesellschaft mbH, Weinheim, S. 65,79 (1987)), or to prepare other chiral 2,4-disubstituted 1,3-dioxolanes.

The steric tension of the anhydrosugar allows it, or its derivatives, to react, e.g. trialkylethers with suitable catalysts to 1,6-linked polymers (Polymer J. Vol. 16, No. 3 pp 297–30.1 (1984); Vysokomol. Soedin., Ser. A 1984, 26 (10), 2173–80, cit. in Chem. Abstr. 102, 95 916q); derivatives of levoglucosan are used, too, for three-dimensional polymerization (SU 862 567, cit. in Chem. Abstr. 101, 73 215 n; SU 1 038 344, cit. in Chem. Abstr. 100, 175 205f).

Different ways are known for the preparation of levoglucosan, e.g.:

a) the pyrolysis of starch (Methods Carbohydr. Chem. 2, 394 (1963)), b) the reaction of phenyl-2,3,4,6-tetra-0-acetyl-β-D-glucopyranoside with alkali (Methods Carbohydr. Chem. 2, 397 (1963)), c) the reaction of pentachlorophenyl-2,3,4,6-tetra-O-acetyl-β-D-glucopyranoside with tetrabutylammoniumhydroxide (Carbohydr. Res. 101, 148 (1982)), d) the pyrolysis of acid-treated (e.g. with monochloroaceticacid) hard-wood with superheated steam (SU 1 133 279, cit. in Chem. Abstr. 102, 204 235q, (1985)), e) the base-catalyzed elimination of hydrogen fluoride from α-D-glucopyranosylfluoride (comp. Phytochemistry 21, 2301 (1982)), f) the pyrolysis of pretreated starch (U.S. Pat. No. 3,478,012) and g) the pyrolysis of acid or base pretreated cellulose with super-heated steam, preferably between 350 and 600° C., and work-up with organic solvents (U.S. Pat. No. 3 235 541).

Other methods have to be mentioned:

h) In a more recent synthesis of levoglucosantriacetate (carbohydrates are prepared often as acetates because of the simpler isolation) 1,2,3,4-tetra-O-acetyl-6-O-triphenyl-methyl-β-D-glucopyranose is reacted with several Lewis-acids, whereby in some cases high yields of levoglucosantriacetate are achieved (Carbohydr. Res. 162, 141 (1987)).

i) Purification procedures of levoglucosan-containing mixtures are described e.g. in Mater. Nauch.-Tekh. Konf. Khim.-Tekhnol. Fak., Leningrad. Lesotekh. Akad. 1967, 90, cit. in Chem. Abstr. 71, 82 868s. A salt removal with acid and basic ion-exchangers yields indeed a decoloration of the raw solution, but the efficiency of the anion-exchanger is soon diminished. An alternative method, the fractional precipitation of levoglucosan from butanolic solutions with diethylether requires the use of expensive and dangerous organic solvents.

k) In U.S. Pat. No. 3,374,222 a levoglucosan-containing solution prepared by pyrolysis of wood or lignocellulosic material, is brought to a pH-value of 12 or higher. By several steps as cooling, diluting, heating, filtering, one gets at the end levoglucosan-containing aqueous solutions which can be desalted, too, by the aid of acid and basic ion-exchangers.

The utilisation of organic solvents, such as amylalcohol, ethylacetate or diethylether, for pre-purification of the aqueous phase is pointed out.

l) Also, in recent processes (SU 1 155 604, cit. in Chem. Abstr. 104, 34 285c (1986)) the purification of levoglucosan and its crystallization from acetone and its recrystallization from 90–96% ethanol at 15–30° C. is described.

For a large scale production of levoglucosan in high purity the known procedures are too complicated and/or too expensive. As a cheap starting material starch is very well suited.

The disadvantages of the known starch pyrolysis are the following (Methods Carbohydr. Chem. 2, 394 (1963)):

1. The applied powdery starch is dried thoroughly at 100° C. for 24 hours with occasionally mixing. This is troublesome and expensive.

2. The pyrolysis in a glass apparatus with the aid of a gasburner leads to layers, which have a bad influence on heat transfer and which makes it necessary to break up the mass occasionally to improve the contact and the heat transfer from the reactor wall.

3. The distillate, a dark brown syrup, is twice concentrated to dryness with the aid of relative great amounts of acetone and under diminished pressure. The residue is dissolved in acetone and held at 0–5° C. overnight after addition of seeding crystals. The raw dark brown crystals are separated, repeatedly washed with acetone, dried and recrystallized in hot methanol with added active carbon, whereby a technical product is formed. The last purification is made via the triacetate, which is deacetylated with sodium methylate in methanol, desalted and the solid is recrystallized from methanol.

Not least of these complicated procedures, the alkaline treatment of phenyl-$\beta$-D-glycopyranoside is mentioned as the best-known synthesis of levoglucosan in a review in Adv. in Carbohydr. Chem. Biochem. 39-, 157 (1981). About the pyrolysis as method for preparing 1,6-anhydrosugars is written: 'A variety of by-products and a char are usually formed; lengthy purifications and slow crystallizations are not unusual. Negative catalysis, variable results and unpleasant esthetics discourage casual use of this method . . . '

As in many other chemical processes too, the isolation of levoglucosan from the reaction mixture is the crucial problem of the method of preparation of a pure product, because the pyrolysis of a polymer, such as starch, leads to a broad product spectrum.

In Adv. in Carbohydr. Chem. 34, 23 (1977) a number of more than 37 compounds of low molecular weight, which are volatile, is mentioned which are produced in a pyrolytic reaction. Among these are such different substances as furfural, furan, acetaldehyde, acetone, acrolein, formic and acetic acid.

Therefore recent syntheses start with derivatives of the monosaccharide glucose, e.g. glycosides.

A method to prepare the desired levoglucosan in good yield, starting with a good, accessible renewable raw-material, such as starch, and using a simple reaction and a simple work-up, would be therefore a big improvement due to the versatility of this simple glucose derivative.

In the instant inventive process the preparation of levoglucosan in crystalline form in good yield and high purity with water as the single solvent, was achieved by making use of a) a suitable method of pyrolysis (depolymerization) of starches and/or starch- or cellulose-containing material, b) a chromatographic work-up of the distillate with the aid of ion-exchangers, a method which is used today industrially in ton-scale and c) an evaporation - and/or cooling crystallization of levoglucosan-containing syrups.

Measures to be observed follow the claims description.

It is surprising, that with such simple means levoglucosan can be recovered in such a high purity even on a large-scale and an economical way.

In the inventive process starch-containing raw-materials, e.g. commercial starch with an average water-content up to 14% or wheat flour type 812, is brought into a pyrolysis apparatus of metal, so, that a layer of 1–10 cm thickness covers the bottom uniformly.

The water-content can be brought to max. 20% by adding water, thus facilitating the formation of a layer of equal level.

Figure 1:
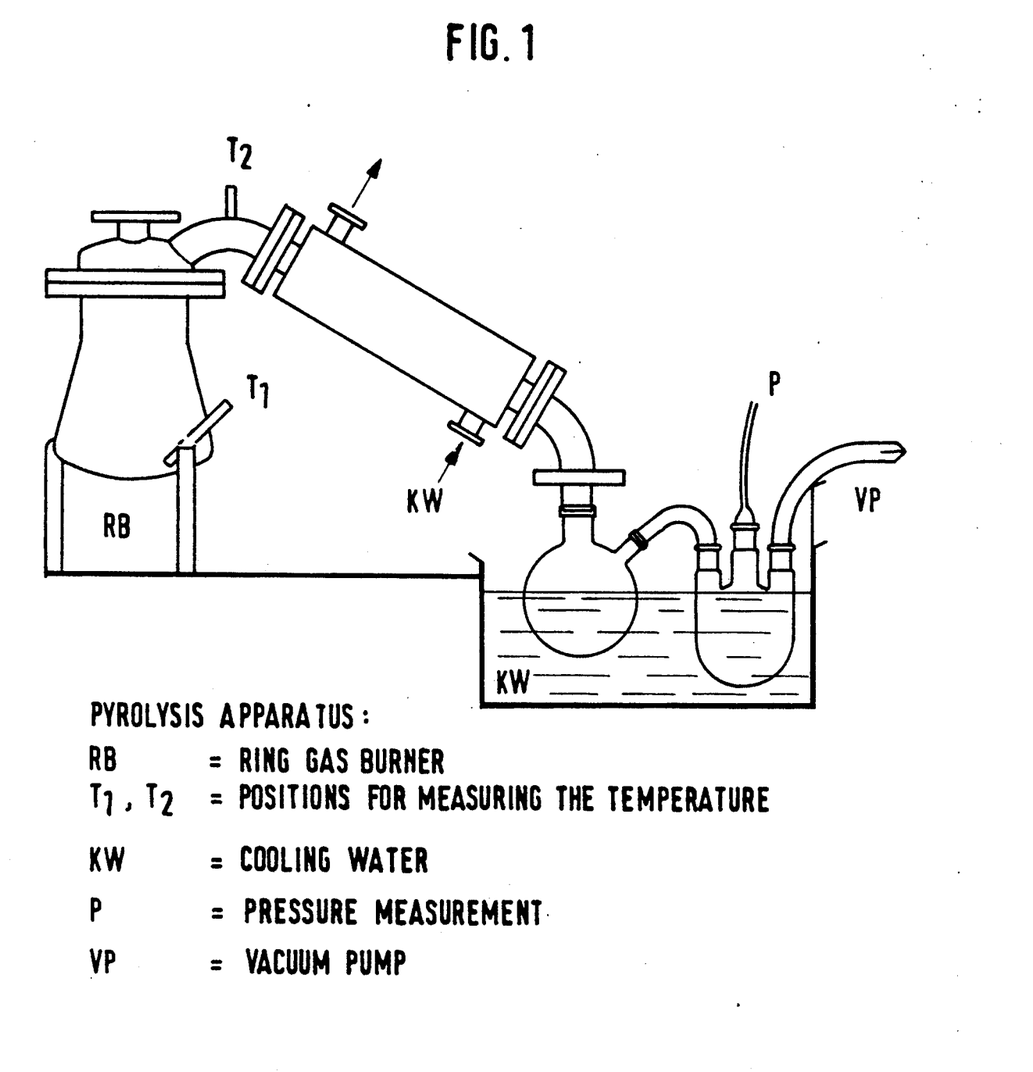
Figure 2:
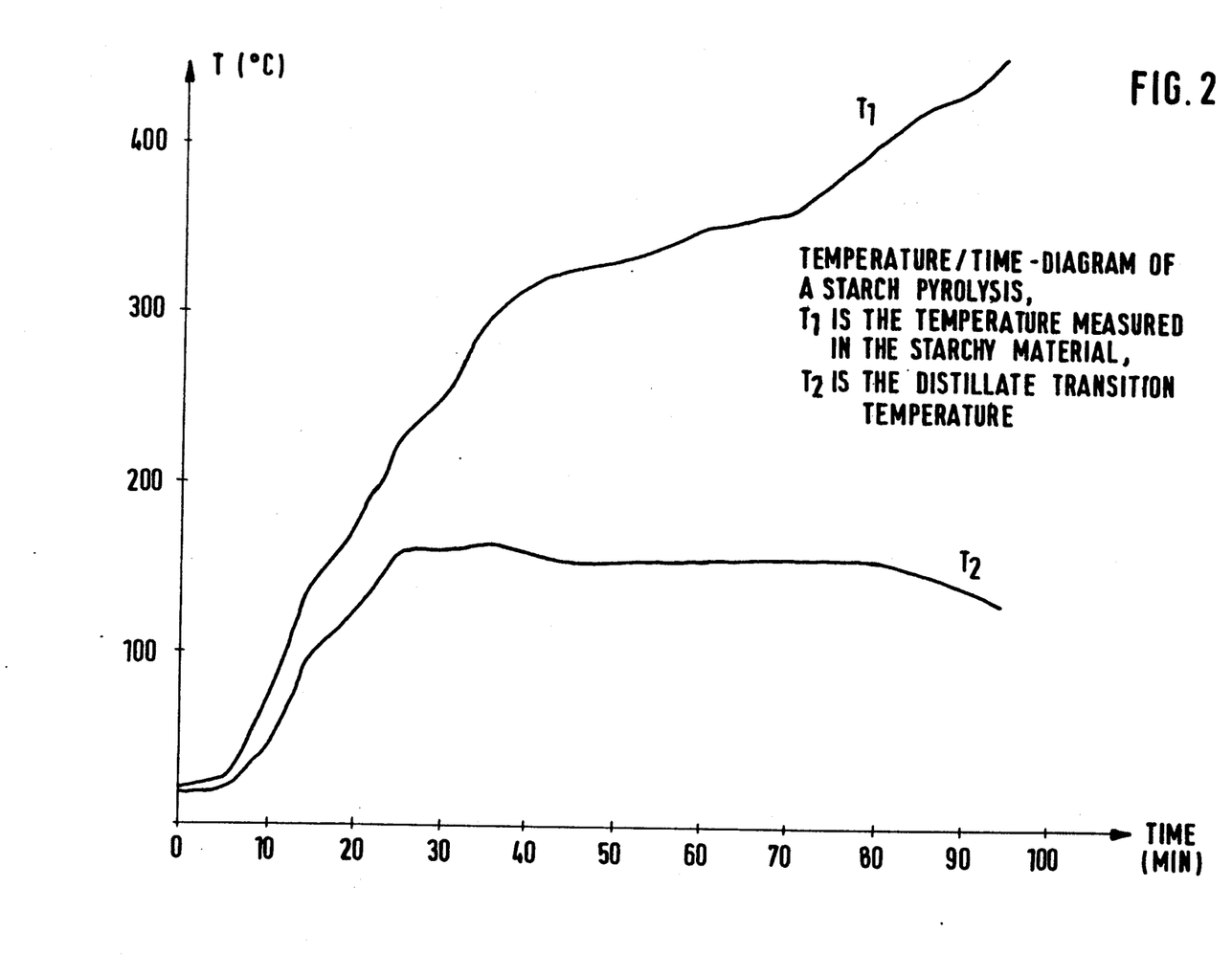

The apparatus (FIG. 1) is slowly evacuated until a pressure of 0.0015–6.67 kPa, preferably 2.00–3.34 kPa, is reached. Then the bottom of the pyrolysis apparatus, is heated, e.g. with a ring-gas-burner with a suitable diameter. An exemplary time/temperature diagram is shown in FIG. 2. The temperature in the cooler is controlled so that the condensate has a temperature between 30° and 90° C. and so is well flowable. Two flasks, one behind the other are cooled additionally by immersing in a water basin. The final temperature in the pyrolyzed mass should be preferably about 430°–470°C., which enables easy cleaning and removing of the residue.

The coloured aqueous distillate has a pH value of about 3 due to the volatile acids and is neutralized immediately to pH 6 to 8 with a base in solid form or as an aqueous solution, after cooling and relieving the vacuum in the apparatus. The mode of adding base depends appropriately on the salt-form of the ion-exchange resin used for the following chromatography.

If e.g. the ion-exchanger material for the chromatographic separation is in $Ca^{2+}$-form, it is advantageous to neutralize the distillate of the pyrolysis with Ca(OH)$_2$ or $CaCO_3$.

The treatment of the filtered and/or neutralized solution with an adsorbent, e.g. active carbon for the removal of high-molecular impurities, prolongs the lifetime of the chromatographic resin.

An advantage of the inventive process is that the aqueous solution (distillate from the pyrolysis) results in 35–70% dry substance, which is an advantageous concentrational range for a preparative chromatography i. e. one would rather dilute the solution with water than to concentrate it.

The chromatographic separation is accomplished with water as eluent at a temperature between 20° and 100° C., preferably between 30° and 95° C., especially preferably between 50° and 70° C., and a linear flow rate of 2–8 cm/min, preferably 3–5 cm/min (comp. exemp. 1 pyrolysate A and B).

As chromatographic resins there can be used cation-exchangers in monovalent salt form (e.g. $Na^{3+}$), in bivalent form (e.g. $Ca^{2+}$) or in trivalent form (e.g. $Al^{3+}$). The ion-exchangers can be e.g. strongly acid, highly cross-linked, macroporous cation-exchangers based on polystyrene sulfonic acid (e.g. Lewatit SP 112), or weakly acid, macroporous cation-exchangers based on polyacrylate (e.g. Lewatit CNP LF) or strongly acid, weakly cross-linked, gelous cation-exchangers (e.g. Lewatit TSW 40). Moreover, other cation-exchangers are suitable in the inventive process.

Advantageously, colored material and ionic impurities are eluted markedly before levoglucosan-containing fractions, which are indicated by a negative rotational value at the polarimeter.

According to the invention levoglucosan can be prepared pure, too, by an ion-exchange chromatography from reaction mixtures which are produced from other raw-materials e.g. cellulose or glycosides and in other processes e.g. base-catalyzed HF-elimination from $\alpha$-D-glucopyranosylfluoride and which are aqueous feeding solution of a chromatography.

These processes can be practiced both batch wise and continuously (comp. Die Stärke 22, 221 (1970)).

Resulting fractions from the chromatographic separation with a levoglucosan-content of >75%, in the dry substance, are combined and concentrated in vacuo or at ambient pressure at a temperature up to 110° C.

Figure 3:
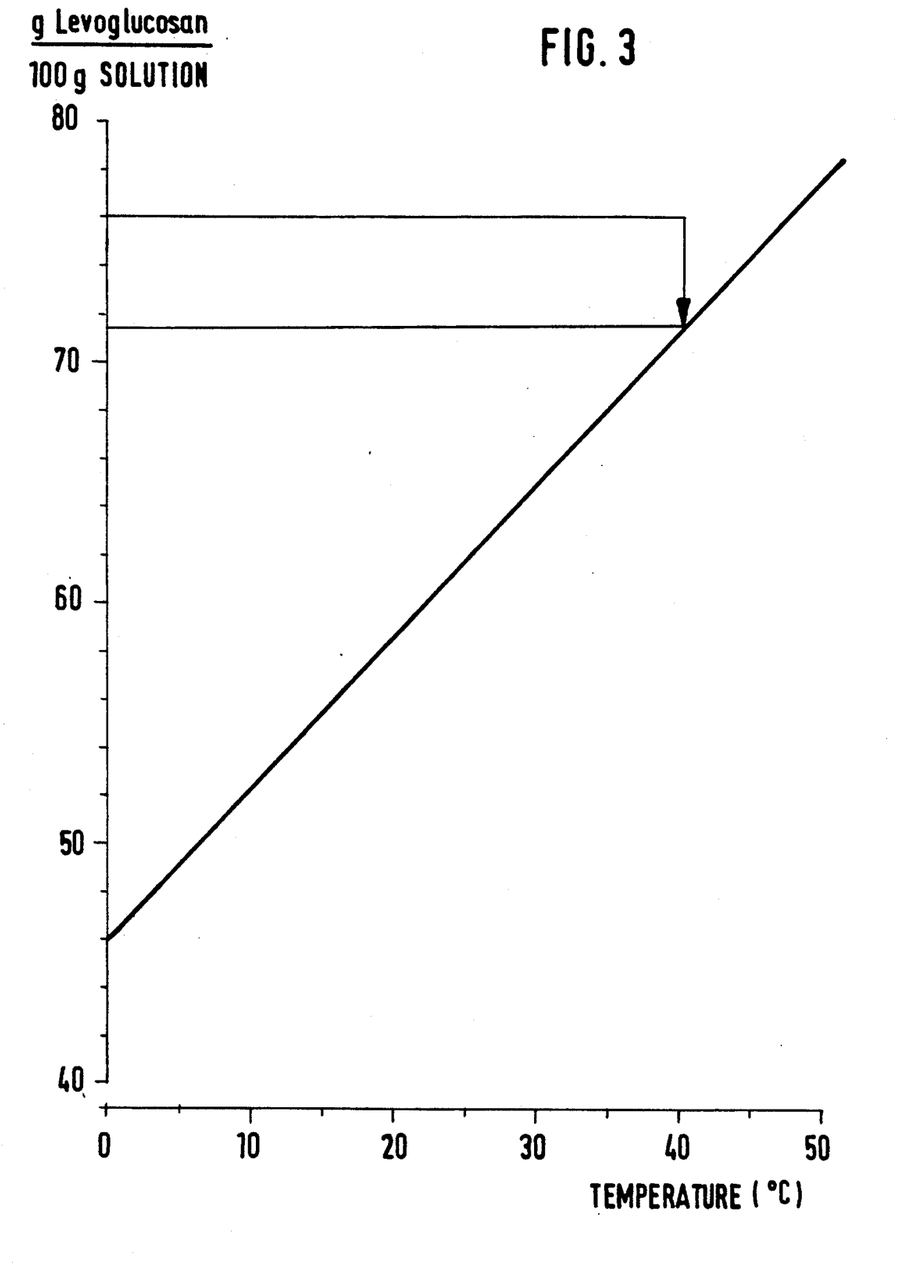

In a vacuum-evaporation crystallizer the concentrated levoglucosan-containing syrup is slightly super-saturated by water evaporation, e.g. 76% (D. S.) at 40° C., super-saturation of about 1.06 (comp. FIG. 3), then seeding crystals are added and the super-saturation is reduced isothermally accompanied by stirring, leading to a crystal-growth.

By feeding the syrup to be crystallized with simultaneous evaporation of water, a crystal magma is formed, which is separated, after termination of the crystallization, in a filter centrifuge into crystals and mother liquor.

Figure 4:
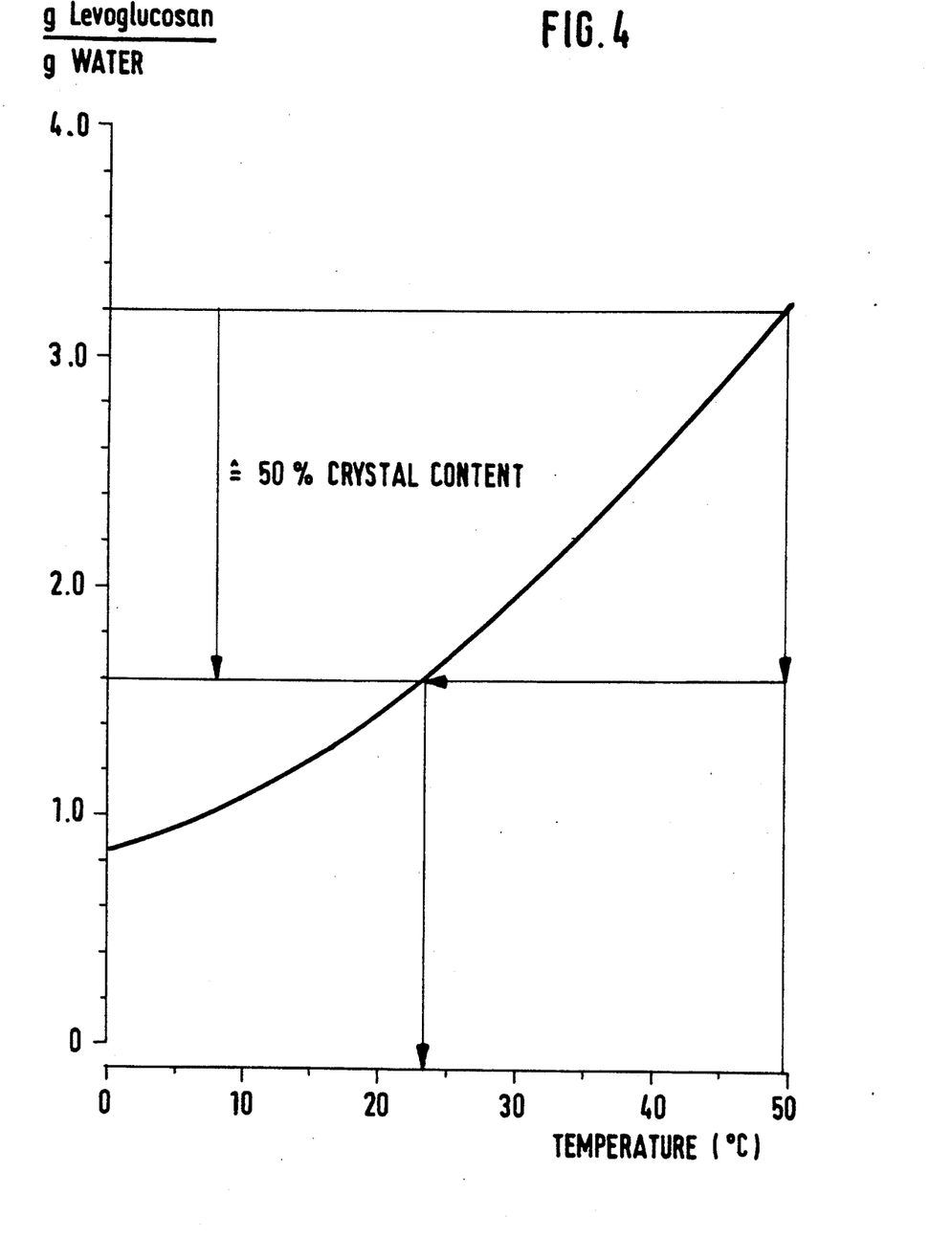

Alternatively, a crystal suspension can be produced too, by a cooling crystallization after seeding with crystals at the saturation point and slow cooling to that temperature at which e.g. a 50% crystal yield is reached (comp. FIG. 4), followed by separation of this suspension in a filter centrifuge or in a nutsche into crystals and mother liquor.

Also, a combination of evaporating and cooling crystallization is possible, by producing first of all a magma in an evaporating crystallization at elevated temperature (ca. 80° C.) followed by cooling the crystal suspension to room temperature under stirring.

The high purities of levoglucosan containing solutions produced in the inventive chromatograpic separation are the reason that one obtains coarse-grained, well-centrifugable crystals which possesses a high purity even after only one crystallization.

EXAMPLE 1

Pyrolysis 3 kg of commercial starch with a water-content of 14% is introduced into pyrolysis apparatus of metal in such a way that a layer of constant level (ca. 8 cm) covers the slightly concave formed bottom. It is possible to measure the temperature in the pyrolyzing mass and in the distillate transition. The cooler, too, is of metal. The mass to be pyrolyzed is with a suitable ring-gas-burner, after the whole apparatus has been evacuated with a steam blast nozzle pump to a pressure of about 3.34 kPa. An exemplary time/temperature diagram is shown in FIG. 2.

The end of the reaction is reached when the temperature in the material comes to 450–470° C. and the temperature of the distillate transition decreases.

After cooling and removing the vacuum of the apparatus, the cooler is rinsed with steam, so transferring traces of the sirupy distillate to the receiving flask.

The pyrolyzate (about 2.1 kg) has a pH-value of about 3 and is brought, with calcium hydroxyde (about 60 g), to pH 6.5, and then is filtered with a filter aid, e.g. kieselgur and subsequently chromatographed.

Starting with 3.0 kg starch one obtains 2.74 kg of filtered and neutralized distillate with a refractive index of 1.444 (61% dry substance) and a levoglucosan content of 59% referred to the dry substance content and determined by HPLC (column length 30 cm, material BIO-RAD HPX-87C, eluent: water, temperature 85° C., flow rate 0.5 ml/min).

The determination of levoglucosan concentrations in aqueous solutions is made by measuring the refractive index according to schedules from Latv. PSR Zinat. Akad. Vestis Kim. Ser. 1967 (1), 119-221 (cited in Chem. Abstr. 67, 50 437b).

Chromatography of starch pyrolyzates A

The combined distillates of some pyrolysis reactions are treated with activated carbon and are fed, as a 47% (D.S.) aqueous solution (18.5 kg) at a temperature of 65° C., to chromatographic column equipment. This contains a sulfonated, divinylbenzene cross-linked polystyrene resin in $Ca^{2+}$-form. The ion-exchanger is strongly acidic and gelatinous. The equipment contains three columns, inner diameter 25 cm, with a total capacity 500 l.

With de-ionized water, the columns are eluted at 65° C. to produce a partial stream of the elution stream, coming from the third column which flows through a refractometer, a polarimeter and a conductivity measuring instrument, and the data are recorded. The result is shown in diagram FIG. 5.

The extinction data were measured at 420 nm subsequently in single fractions. The extinction at 420 nm is a measure of the colour of the solution.

As can be seen, ionic (conductive) and coloured impurities can be well separated before the levoglucosan fraction is identified by negative values at the polarimeter.

The feed solution contains 63.2% levoglucosan and 36.8% impurities, related to the dry substance content. The individual fractions 1-14 (2.42 kg estimated by refractive index) are discarded, fractions 15 and 16 are combined and re-chromatographed and the product fraction (individual fractions 17-23, 4.82 kg determined by refractive index) is concentrated and crystallized by evaporation.

Chromatography of starch pyrolyzates B

Figure 6:
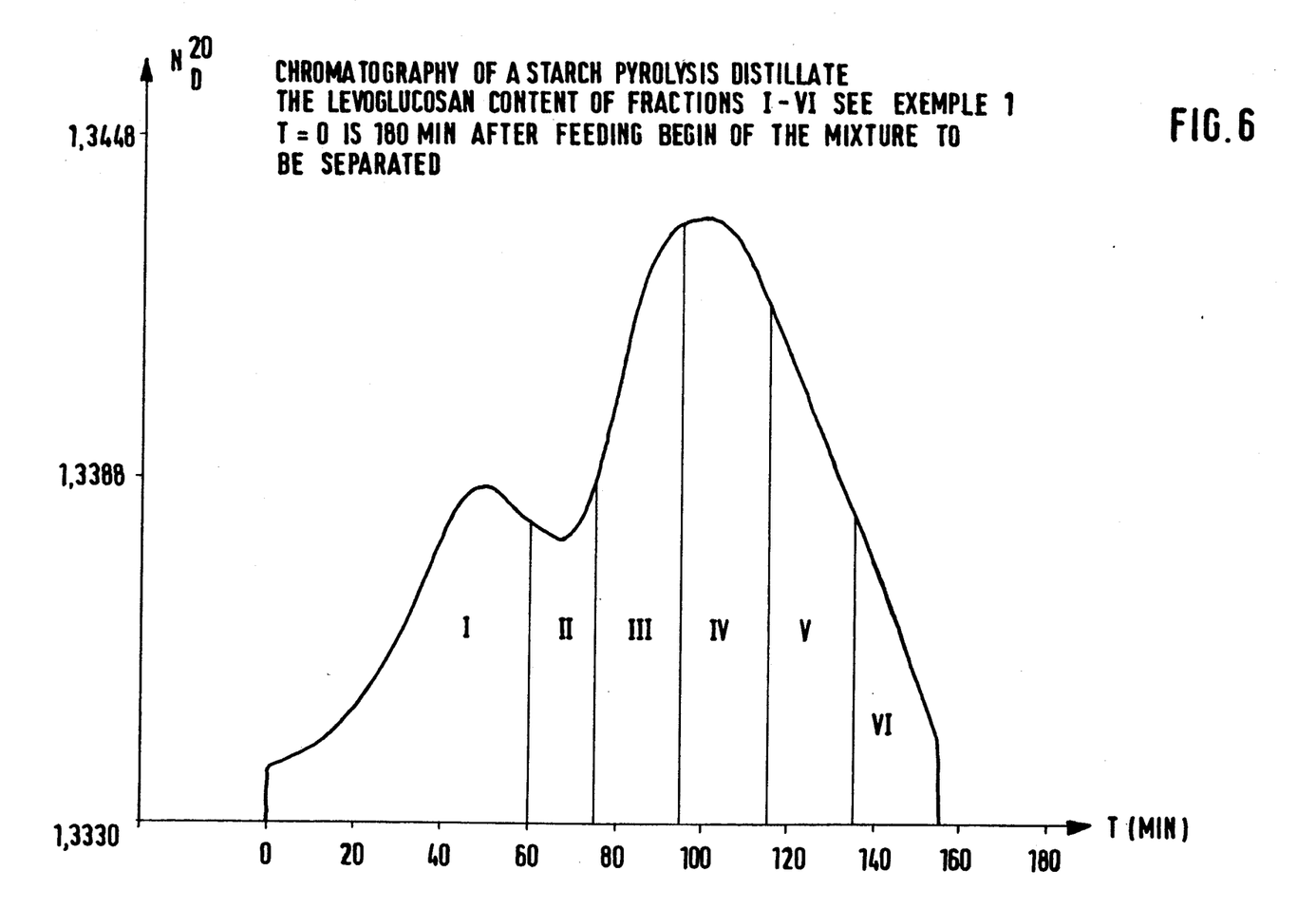

The composition of a chromatography analogous to chromatography A is shown in FIG. 6. The feed solution contained 63.8% levoglucosan, total amount 11.5 kg of dry substance as 30% aqueous solution. The fractions I-IV contain:

| Fraction I   | 0%    | levoglucosan with $n_D^{20} = 1.3358$ |
|--------------|-------|----------------------------------------|
| Fraction II  | 14.5% | levoglucosan with $n_D^{20} = 1.3375$ |
| Fraction III | 75.8% | levoglucosan with $n_D^{20} = 1.3423$ |
| Fraction IV  | 93.4% | levoglucosan with $n_D^{20} = 1.3417$ |
| Fraction V   | 96.6% | levoglucosan with $n_D^{20} = 1.3400$ |
| Fraction VI  | 90.6% | levoglucosan with $n_D^{20} = 1.3352$ |

Fraction I is discarded, fraction II is rechromatographed and fractions III-VI are combined, concentrated and crystallized by evaporation.

Crystallization

The obtained fractions from the chromatographic separation III-V (see example above) are concentrated in a thin-film evaporator to a dry substance content of about 50% (14.2 kg with $n_D^{20} = 1.4173$).

In a rotational evaporator, a part is further concentrated in vacuo to a concentration of 80%, seeded at 45° C. with crystals of levoglucosan, and water is further evaporated until there is a visible crystal growth (~10 min). The main part of the combined fractions III-V is slowly fed to the crystal magma. Subsequently, the crystal suspension is slowly, under stirring, cooled to room temperature and with the aid of a filter centrifuge separated into crystals (3.28 kg, purity 98.8%) and mother liquor (3.65 kg).

The mother liquor is combined with fraction VI and crystallized (as above). One obtains 2.17 kg crystals with a purity of 99.0% together with 3.67 kg of a mother liquor having a refractive index of 1.4514. The mother liquor is rechromatographed. The initial solution contained 7.23 kg levoglucosan. The total crystal yield of levoglucosan is 5.45 kg (75.4%). The crystals had a purity >98.8% and a melting point of 175 ° C.

EXAMPLE 2

Chromatography of a distillate obtained by wheat flour pyrolysis 847 g of a distillate with a refractive index of 1.3776 corresponding to about 240 g dry substance, obtained by the pyrolysis of wheat flour type 812 and subsequent treatment with active carbon (levoglucosan content determined by HPLC as 41.6% related to dry substance) is chromatographed with water as eluent at 70 ° C. over a column (length 200 cm, inner diameter 8 cm, containing Lewatit TSW 40 in $Ca^{2+}$-form).

Figure 5:
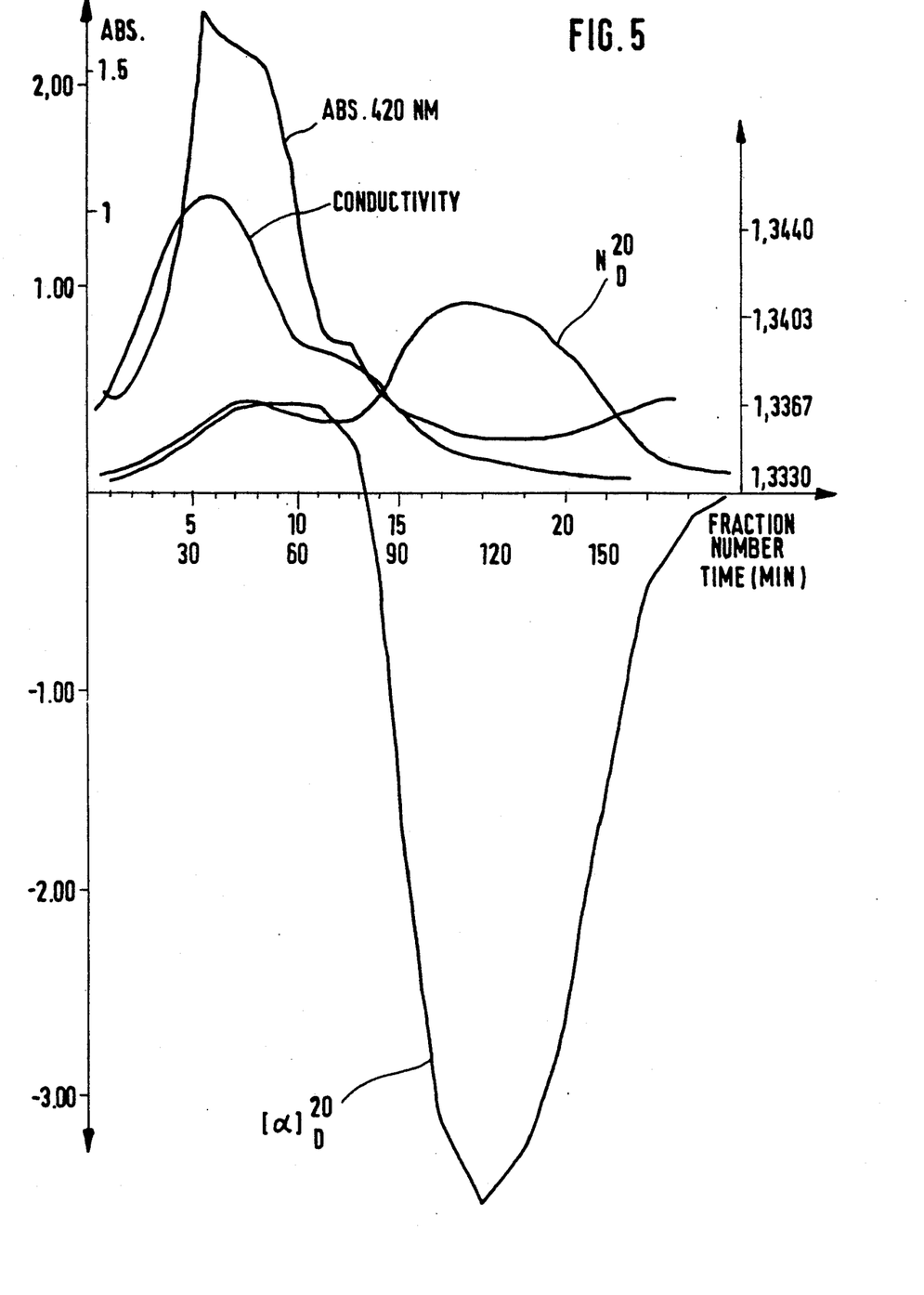

The chromatogram is similar to that shown in FIG. 5. Reaching a refractive index $n_D^{20}=1.335$ in the eluate, fractions are collected in 0.5 l portions. Fraction 9 (73.8% levoglucosan), fraction 10 (79.8% levoglucosan), fractions 11 (87.8% levoglucosan) and fractions 12 (74.3% levoglucosan referred to D. S.) are combined and crystallized.

A simple and fast method to detect highly enriched levoglucosan-containing fractions is thin-layer chromatography on silica gel 60 $WF_{254}$ s, eluent $CH_3CN/H_2O$:80/20, detection: charring, $R_f$ value: 0.48.

We claim:

1. A process of preparing 1,6-β-D-anhydroglucopyranose (levoglucosan) in high purity comprising:

vacuum pyrolyzing, at a pressure of less than 13.34 kPa, at least one material, having a water content of up to about 20%, selected from the group consisting of starch containing materials, and cellulose containing materials at a temperature of greater than about 150° C. to produce a levoglucosan containing volatile pyrolysis product;
    condensing the volatile products of said pyrolysis;
    neutralizing said condensate, with a base, to a pH of about 6 to 8;
    chromatographically separating said neutralized condensate with water at about 20–100° C. in contact with a substantially neutral ion-exchanger selected from the group consisting of sulfonated polystyrene and polyacrylate, whereby eluting salts and high molecular weight materials prior to eluting the levoglucosan containing fraction;
    concentrating the levoglucosan containing fraction; and
    crystallization levoglucosan from said concentrated fractions.

2. A process as claimed in claim 1, wherein said crystallization is accomplished by evaporation of water from at least some of said concentrated fractions.

3. A process as claimed in claim 1, wherein said crystallization is accomplished by cooling at least some of said concentrated fractions.

4. A process as claimed in claim 1, including filtering said neutralized condensate.

5. A process as claimed in claim 1, wherein said material for pyrolysis is a powdery starch with a water content of about 10 to 18%, and including, prior to said pyrolysis, adding water thereto to produce a pyrolyzable material having up to about 20% water.

6. A process as claimed in claim 1, including forming said material to be pyrolyzed into a layer of about 1 to 10 cm in height and pyrolyzing such at a pressure of about 0.0013 to 13.34 kPa.

7. A process as claimed in claim 6, wherein said pressure is about 2 to 3.34 kPa.

8. A process as claimed in claim 1, including pyrolyzing at a temperature of about 200 to 500° C.

9. A process as claimed in claim 8, wherein said temperature is about 200 to 470° C.

10. A process as claimed in claim 1, including absorbing high molecular weight material in said neutralized condensate prior to said chromatographic separation.

11. A process as claimed in claim 10, wherein the absorbent is activated carbon.

12. A process as claimed in claim 1, wherein the cation of said ion exchange resin, and the cation of the neutralizing agent are substantially the same.

13. A process as claimed in claim 1, wherein said ion exchange resin comprises a strongly acid macroporous polystyrene sulfonic acid.

14. A process as claimed in claim 1, wherein said ion exchange resin comprises a weakly acidic macroporous polyacrylate.

15. A process as claimed in claim 1, wherein the temperature of said chromatography is about 50 to 70° C.

16. A process as claimed in claim 1, including concentrating said levoglucosan containing fractions to a supersaturation in water of about 1.01 to 1.1.

17. A process as claimed in claim 1, including chromatographically separating mother liquor resulting from said crystallization to produce additional levoglucosan containing fractions.

18. A process of claimed in claim 17 including combining multiple mother liquors prior to separating such.

19. A process as claimed in claim 17, including combining said mother liquor with at least one chromatographically separated fraction containing less than about 75%, based on dry weight, of levoglucosan prior to separating such.

20. A process as claimed in claim 1 wherein said ion exchanger comprises a resin comprising a strongly acidic, weakly crosslinked gelatinous material.

* * * * *